US00PP16305P2

(12) United States Plant Patent
Bremner

(10) Patent No.: US PP16,305 P2
(45) Date of Patent: Mar. 7, 2006

(54) ***GERANIUM* PLANT NAMED 'SABANI BLUE'**

(50) Latin Name: ***Geranium libani×ibericum* ssp. *jubatum***
Varietal Denomination: Sabani Blue

(76) Inventor: Alan Heddle Bremner, Bendigo St. Ola, Kirkwall Orkney (GB), KW15 ISX ( * ) Notice: Subject to any disclaimer, the term of this patent is extended or adjusted under 35 U.S.C. 154(b) by 163 days.

(21) Appl. No.: 10/806,722

(22) Filed: Mar. 24, 2004

(51) Int. Cl.
*A01H 5/00* (2006.01)

(52) U.S. Cl. ..... Plt./324

(58) Field of Classification Search ..... Plt./324
See application file for complete search history.

*Primary Examiner*—Kent Bell

(57) ABSTRACT

A new cultivar of *Geranium* plant named 'Sabani Blue' which carries upward-facing dark blue flowers early in the season and whose foliage forms a tight dome or mound which does not die down in the summer. In combination these traits set 'Sabani Blue' apart from all other existing varieties of *Geranium* known to the inventor.

2 Drawing Sheets

Genus: *Geranium.*
Species: *libani×ibericum* ssp. *jubatum.*
Denomination: 'Sabani Blue'.

BACKGROUND TO THE INVENTION

The present invention relates to a new and distinct variety of hardy *Geranium* grown for use as an ornamental plant for the landscape. The new cultivar is known botanically as *Geranium libani×ibericum* subspecies *jubatum,* and will be referred to hereinafter by the cultivar name 'Sabani Blue'.

The inventor has been a student, collector and breeder of *Geraniums* since 1985. In particular, the inventor has pursued a scientific interest in the botany of *Geraniums* including the possible relationships between its many species which the inventor has acquired and maintained as individual species reference plants. The inventor's *Geranium* breeding program has explored these relationships as potential inter-specific crosses. The breeding program has also aimed to create new and interesting and garden-worthy cultivars with unusual combinations of characteristics, as with the inventor's variety *Geranium* 'Westray' (U.S. Plant Pat. No. 13,716), itself the result of an inter-specific cross.

In 1993, the inventor carried out controlled pollination in the inventor's glasshouse in Orkney Island, Scotland, United Kingdom as follows: An unnamed plant of the species *Geranium libani* (unpatented) was selected as the intended female parent, and its flowers were emasculated and bagged until receptive. Pollen was transferred from bagged donor flowers taken from an unnamed plant of the species *Geranium ibericum* ssp *jubatum* (unpatented) as male parent. The female flowers were re-bagged. Pollination was successful and the harvested seeds were sown in the spring of 1994. The resulting seedlings were grown on and observed and, from these, 'Sabani Blue' was identified and isolated as a single plant with perceived novel characteristics. 'Sabani Blue' was observed during the ensuing years until 1999 when 'Sabani Blue' was first asexually reproduced by division under the inventor's direction and supervision, since which time 'Sabani blue' has remained true to type in all successive generations.

The new variety, 'Sabani Blue' is distinguished by its early flowering, its upward-facing flowers, its tolerance of full sun and its tight mounding foliage.

When compared with the female parent, an unnamed and typical plant of the species *Geranium libani,* 'Sabani Blue' retains its foliage in summer, whereas the foliage of plants of the species *Geranium libani* tends to die back in summer.

When compared with the male parent, an unnamed and typical plant of the species *Geranium ibericum* ssp. *jubatum,* 'Sabani blue' is earlier to flower, by approximately three weeks.

The closest plant known to the inventor, in vigor and overall appearance, to 'Sabani Blue' is the vegetatively propagated sterile hybrid, *Geranium×magnificum* (unpatented) which is derived from the inter-specific cross *Geranium ibericum×Geranium platypetalum. Geranium× magnificum* is considered to be one of the best and easiest to grow of hardy *Geraniums,* and has been assigned an Award of Garden Merit by The Royal Horticultural Society of England. 'Sabani Blue' is three weeks earlier to flower than *Geranium×magnificum.*

SUMMARY OF THE INVENTION

In addition to the detailed observations described further herein, the following general traits have been repeatedly observed and represent the distinguishing characteristics of the new plant 'Sabani Blue'. In combination these traits set 'Sabani Blue' apart from all other *Geraniums* known to the inventor. 'Sabani Blue' has not been tested under all possible conditions and phenotypic differences may be observed with variations in environmental, climatic and cultural conditions, however, without any variance in genotype.

1. *Geranium* 'Sabani Blue' is early flowering.
2. The foliage of *Geranium* 'Sabani Blue' forms a tight dome or mound which does not die down in the summer.
3. The flowers of *Geranium* 'Sabani Blue' are upward facing.

BRIEF DESCRIPTION OF THE DRAWINGS

The accompanying color drawings illustrate the overall appearance of the new cultivar 'Sabani Blue' showing the colors as true as it is reasonably possible to obtain in colored reproductions of this type. Colors in the drawings may differ from the color values cited in the detailed botanical description which accurately describe the actual colors of the new variety 'Sabani Blue'.

The drawing of 'Sabani Blue' labeled as FIG. 1 depicts a mature plant which is approximately 2 years old from a division and which has been grown in an open border in a garden in Cambridgeshire, United Kingdom.

Figure 1:
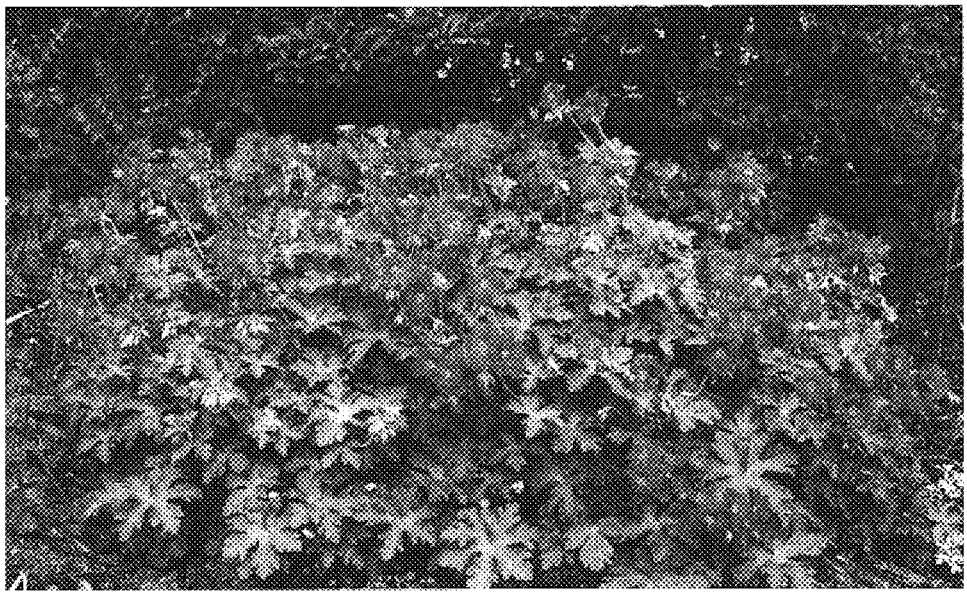
Figure 2:
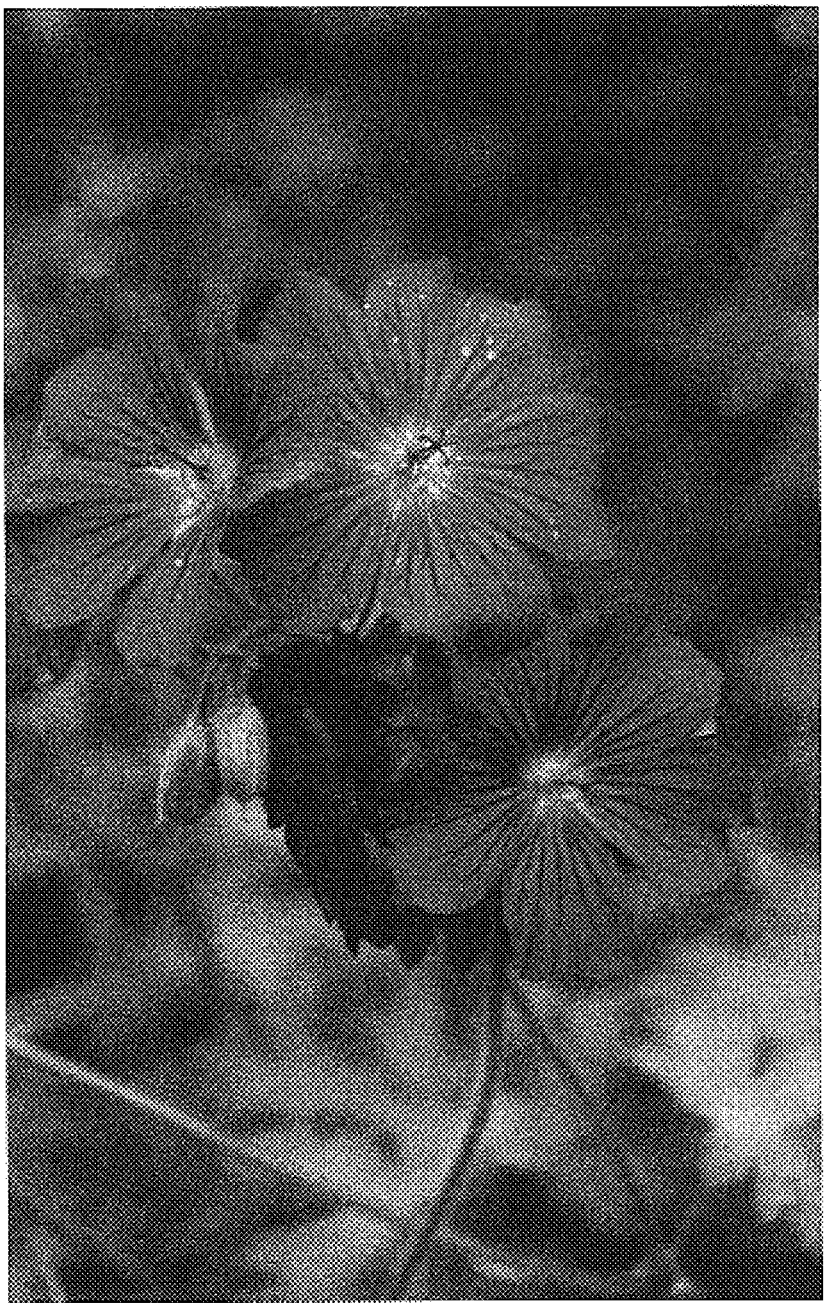

The drawing labeled as FIG. 2 depicts a close-up view of the flower and bud of 'Sabani Blue'.

Both drawings were made using conventional techniques and although colors may appear different from actual colors due to light reflectance they are as accurate as possible by conventional photography.

BOTANICAL DESCRIPTION OF THE PLANT

The following is a detailed description of the new *Geranium* plant named 'Sabani Blue'. Data was collected in Cambridgeshire, United Kingdom, from 2 year old plant growing in open border soil. The color determinations are in accordance with the 2001 Edition of The Royal Horticultural Society Colour Chart of The Royal Horticultural Society, London, England, except where general color terms of ordinary dictionary significance are used.

Botanical classification: *Geranium libani×ibericum* ssp. *jubatum* 'Sabani Blue'.

Species: *Libani×ibericum* ssp. *jubatum.*

Sexuality: Nominally hermaphrodite though some stamens in most flowers are not fully formed; anthers vestigial or absent.

Commercial classification: Hardy perennial.

Common name: Hardy *Geranium.*

Use: Ornamental for container or garden: best positioned in full sun.

Cultural requirements: Plant in well-drained moderately fertile soil in full sun.

Root system: Thick rootstock with fibrous roots.

Parentage: *Geranium* 'Sabani Blue' is an induced hybrid resulting from the controlled pollination of:

*Male parent.*—An unnamed single plant of the species *Geranium ibericum* ssp. *jubatum.*

*Female parent.*—An unnamed single plant of the species *Geranium libani.*

Plant description:

*Bloom period.*—Commencing mid to late April and continuing until September. Lastingness of an individual flower: Approximately 5–7 days in spring and fall; 3–4 days in summer.

*Plant habit.*—Upright, dense and mounding.

*Height.*—Within the range 570 mm to 650 mm.

*Width.*—Approximately 700 mm.

*Hardiness.*—USDA Zone 6.

*Propagation.*—Propagation is accomplished by division.

*Time for a division to establish.*—If divided in spring, a division with a single eye will begin to root within 2–3 weeks and will be an established growing plant in 4–6 weeks after division.

*Crop time.*—3–4 months are needed to produce a finished plant in a 1-liter container.

Pest and disease susceptibility or resistance: Largely unaffected by pest or disease problems although no specific resistances have been established.

Basal stem: Inconspicuous.

Flowering stem:

*Overall length.*—530 mm–655 mm.

*Number of nodes.*—Typically approximately 5.

*Internode length.*—Highly variable, ranges from 50 mm to 205 mm.

*Stem diameter.*—Ranges from 4.7 mm–6.1 mm at lowest internode to 2.5 mm–3.5 mm at higher and highest internode.

*Stem shape.*—Cylindrical.

*Stem color* (*lowest internode*).—Greyed-purple 185D but paler towards base and tending to yellow-green 145B and 145C towards first node.

*Stem color* (*higher and highest internode*).—Yellow-green 145A but slightly less yellow.

*Stem surface.*—Moderately to densely pubescent; hairs eglandular.

*Development of laterals.*—At each node, two laterals developed more or less equally. Terminal flower suppressed except at uppermost node.

Leaves: Flowering stem leaves similar except for leaf and petiole dimensions all of which decrease from basal leaves to uppermost leaves as distinguished below.

*Shape.*—Orbicular.

*Division.*—Seven divisions, extending three-fourths of the way towards midpoint; broadest one-fourth of the way towards the tip. Upper divisions 3-lobed.

*Apex.*—Division tips cuspidate.

*Base.*—Lowest divisions on either side overlapping.

*Venation pattern.*—Palmate.

*Vein color* (*adaxial and abaxial surfaces*).—Green 137A.

*Margins.*—Deeply crenately toothed.

*Attachment.*—Petiolate.

*Petioles.*—Length (basal leaves): 298 mm–393 mm. Length (higher leaves): decreasing towards apex: ranges from approximately 150 mm to approximately 25 mm on uppermost leaf. Diameter (basal leaves): 2.5 mm–3.0 mm. Diameter (higher leaves): decreases towards apex: within range 2.5 mm to 1.5 mm. Color: 143C but browner, strongly tinged with greyed-purple 184A toward the base. Pubescence: Moderate to dense, hairs eglandular.

*Stipules.*—Present. Length: 9 mm–15 mm. Width: 2 mm–5 mm. Color: Papery, transparent, tinged green along midline.

*Arrangement.*—Rosette.

*Leaf surface* (*adaxial surfaces*).—Weakly rugose; sparsely minutely pubescent, hairs eglandular.

*Leaf surface* (*abaxial surfaces*).—Sparsely pubescent, mainly along the ribs, hairs eglandular.

*Leaf dimensions.*—Basal leaf: Length: 105 mm–139 mm. Basal leaf: Width: 103 mm–148 mm. Higher leaves: size decreasing towards apex: ranges from approximately 80 mm length, 80 mm width to (uppermost leaf) approximately 35 mm length, 35 mm width.

*Leaf color* (*adaxial surface*).—137A but slightly yellower.

*Leaf color* (*abaxial surface*).—138B but deeper and slightly browner.

*Fragrance.*—Absent.

Flowers:

*Flowering stem.*—Compound cyme with flowers suppressed at lower nodes.

*Number of flowers per stem.*—In the range 18–67.

*Inflorescence.*—Where present at higher nodes, 1–2 flowered cymules. All stems terminate in compound cyme of 4–9 flowers.

*Bud shape.*—Oval-elliptical.

*Bud length.*—12 mm–13 mm.

*Bud diameter.*—5 mm–6 mm.

*Bud color.*—Varies between 139C and 139D, with protruding petal tips violet-blue N89A.

*Peduncle length.*—On 2-flowered cymules: 59 mm–98 mm. Final internode length to terminal cyme: 63 mm–99 mm.

*Peduncle diameter.*—On 2-flowered cymules: approximately 1 mm. Final internode to terminal cyme: 1.5 mm–2.1 mm.

*Peduncle color.*—145A.

*Peduncle surface.*—Moderately to densely pubescent, eglandular (cymules and compound cyme).

*Sexuality.*—Nominally hermaphrodite though some stamens in most flowers are not fully formed; anthers vestigial or absent.

*Flower shape.*—Saucer-shaped.

*Flower dimensions.*—Depth of throat (corolla): 7 mm–9 mm. Diameter (corolla): 42 mm–47 mm.

*Persistent or self-cleaning.*—Corolla self-cleaning.

*Aspect.*—Upward to nodding.

*Petals.*—Five, unfused.

*Petal shape.*—Obcordate with shallow terminal notch.

*Petal apex.*—Emarginate.

*Petal margin.*—Entire, weakly waved.

*Petal dimensions.*—Length: 21 mm–24 mm. Width: 18 mm–20 mm.

*Petal color* (*adaxial surfaces*).—Violet N88B but paler with veins nearest purple N79B. Basal one-eighth of surface white, N155C but less yellow.

*Petal color* (*adaxial surfaces*).—Between Violet N88A and N88B with veins nearest violet 83A. Basal one-eighth of surface between 76B and 76C.

*Petal surfaces.*—Both smooth.

*Calyx diameter.*—20 mm–22 mm.

*Calyx height.*—3 mm–5 mm.

*Calyx surface.*—Sparsely pubescent, mainly along sepal margins, eglandular.

*Calyx color.*—Sepals green 139D with midvein tending to deeper green 139C and margins tinged red, closest to 53C.

*Sepals.*—Number: Five.

*Sepal shape.*—Ovate.

*Sepal apex shape.*—Strongly mucronate.

*Sepal margin.*—Entire.

*Flower fragrance.*—Absent.

Reproductive organs:

*Stamens.*—Number: Ten, although in most flowers some not fully formed, with anthers vestigial or absent. Some flowers with no anthers present.

*Stamen color.*—See anther and filament below.

*Stamen dimensions.*—Filament approximately 5 mm in length, less than 1 mm in width.

*Anthers.*—Vestigial or absent.

*Anther color.*—Where present, appears brownish-yellow.

*Anther shape.*—Linear.

*Anther dimensions.*—Approximately 2.5 mm in length, less than 1 mm in width. Color and Quantity of pollen: None observed.

*Pistil.*—Five, fused.

*Pistil color and shape.*—See stigma, style and ovary below.

*Stigma shape.*—Strongly reflexed.

*Stigma color.*—Nearest to Greyed-Purple 187D.

*Stigma dimensions.*—Approximately 3 mm in length; markedly less than 1 mm in diameter.

*Style shape.*—Linear.

*Style color.*—Nearest to Greyed-Purple 187D.

*Style dimensions.*—Approximately 5 mm in length; less than 1 mm in diameter.

*Ovary position.*—Superior.

*Ovary color.*—Pale green, too small to match. Densely pubescent.

*Ovary shape.*—Narrow ovate.

*Ovary dimensions.*—2 mm. in length and 1.5 mm in width.

Seed production: No seed production has been observed.

It is claimed:

1. A new and distinct cultivar of *Geranium* plant named 'Sabani Blue' as described and illustrated.

* * * * *